United States Patent
Rau et al.

(10) Patent No.: US 11,058,642 B2
(45) Date of Patent: Jul. 13, 2021

(54) TABLETS WITH IMPROVED FRIABILITY

(71) Applicants: Allen Rau, Cincinnati, OH (US); Donald Stadolnik, Centerbrook, CT (US); Melvin Corcino, Centerbrook, CT (US); Freddy Acosta, Centerbrook, CT (US)

(72) Inventors: Allen Rau, Cincinnati, OH (US); Donald Stadolnik, Centerbrook, CT (US); Melvin Corcino, Centerbrook, CT (US); Freddy Acosta, Centerbrook, CT (US)

(73) Assignee: TOWER LABORATORIES LTD, Centerbrook, CT (US)

( * ) Notice: Subject to any disclaimer, the term of this patent is extended or adjusted under 35 U.S.C. 154(b) by 545 days.

(21) Appl. No.: 13/867,308

(22) Filed: Apr. 22, 2013

(65) Prior Publication Data
US 2014/0315719 A1  Oct. 23, 2014

(51) Int. Cl.
*A61K 9/20* (2006.01)
*A61Q 11/00* (2006.01)
*A01N 25/00* (2006.01)

(52) U.S. Cl.
CPC ............ *A61K 9/2031* (2013.01); *A01N 25/00* (2013.01); *A61K 9/2013* (2013.01); *A61Q 11/00* (2013.01)

(58) Field of Classification Search
None
See application file for complete search history.

(56) References Cited

U.S. PATENT DOCUMENTS

| | | | |
|---|---|---|---|
| 3,518,343 A * | 6/1970 | Palermo | A61K 9/2004 424/44 |
| 4,093,710 A | 6/1978 | Sass et al. | |
| 5,403,593 A | 4/1995 | Royce | |
| 6,649,186 B1 | 11/2003 | Robinson et al. | |
| 2005/0013860 A1* | 1/2005 | Venkatesh | A61K 9/2081 424/469 |
| 2007/0286819 A1* | 12/2007 | DeVries | A61K 9/0056 424/48 |
| 2008/0031947 A1* | 2/2008 | Hamed | A61K 9/0056 424/469 |
| 2010/0034889 A1* | 2/2010 | Rau | A23L 2/395 424/489 |
| 2011/0112160 A1 | 5/2011 | Legen et al. | |
| 2011/0135738 A1 | 6/2011 | Legen et al. | |
| 2011/0136883 A1 | 6/2011 | Injae et al. | |
| 2011/0262497 A1 | 10/2011 | Injac et al. | |

OTHER PUBLICATIONS

Cooper et al, Some Information on Tablet Hardness Testing, 2016, Engineering Systems, pp. 1-3. (Year: 2016).*
EPO Search Report, EP, dated Jul. 22, 2014, Tower Laboratories, Ltd.
J.I. Wells, et al., "Improved Wet Massed Tableting Using Plasticized Binder", Jounrl of Pharmacy and Pharmacology, vol. 34, No. S12, Dec. 1, 1982, pp. 46P-46P.
Howard, M.A., et al., "PEO and MPEG in High Drug Load Extruded and Spheronized Beads that are devoid of MCC", International Journal of Pharmaceutics, Elsevier BV, NL, vol. 307, No. 1, Jan. 3, 2006, pp. 66-76.

* cited by examiner

*Primary Examiner* — Trevor Love
(74) *Attorney, Agent, or Firm* — Kelber Law Group; Steven B. Kelber

(57) ABSTRACT

Tablets are prepared with friability reducing agents to yield tablets that are more resistant to breakage or crumbling, but with satisfactory hardness. The friability reducing agents include low molecular weight polyethylene glycol as well as similar agents exhibiting at least three percent (3%) hydroxide moieties and a water solubility of at least eighty percent (80%) (w/w %) in room temperature water. The tablets may comprise an active agent and excipient of almost any type, and about 0.1-about 0.5% by weight friability reducing agent. They exhibit a hardness of at least eighty percent (80%) of the same tablet prepared without the friability reducing agent.

8 Claims, No Drawings

TABLETS WITH IMPROVED FRIABILITY

BACKGROUND OF THE INVENTION

1. Background of the Technology

To those versed in the art and science of tableting, the term friability describes a tablet's propensity to crumble. When a tablet formulation displays high friability, it crumbles easily. This is not a good thing. Highly friable tablets are difficult to convey during production and are hard to package and transport. Consumers, reasonably, expect their tablet products to be unbroken and whole.

This invention is based on the inclusion of lower molecular weight polyethylene glycol (low MW PEG) in tablet formulations. These PEGs are liquid at room temperature (melting points below about 35° C.). They have average molecular weights of about 200 to 800. We have discovered that low molecular weight PEG has the surprising benefit of dramatically improving the friability of tablet formulations.

2. Background of the Prior Art

This performance is not known in the art. In fact, the major manufacturer of PEG, Dow Chemical Company, teaches away from using low MW PEG for tableting in their sales literature (reference dow-answer.custhelp.com: Carbowax™ Sentry™ PEGS & MPEGS for Pharmaceuticals; answer id 3561, Carbowax™ Sentry™ Polyethylene Glycols for Cosmetics and Personal Care (answer id 3541) and Carbowax™ Sentry™ Polyethylene Glycols (form no 118-01790-1011 AMS)). Searches of the United States and European patent literature do not yield results that teach the inclusion of low MW PEG in tablet formulations, let alone for its ability to improve tablet friability.

Polyethylene glycol (PEG) is a polymer frequently used in tablet formulations. Higher molecular weight PEG is commonly used a binder and/or as a lubricant. Typically, PEG with average molecular weight 8000 (INCI nomenclature PEG-180, trade name: Carbowax™ 8000) is used for this function. PEGs with slightly lower MW (down to about MW 4000) are also known to be used for this function. The higher molecular weight PEGs are solid at room temperature and have melting points around 50-60° C. Numerous citations of these materials being used for these functions can be found in the art.

Dow Chemical Company's publication "Carbowax™ Sentry™ Polyethylene Glycols" (form no. 118-01790-1011 AMS, page 8, obtained from the dow.com website) indicates that materials with slightly lower molecular weight, "MW 1450 and higher" can be used as processing aids for granulations. This reference however goes on to state that "high MW materials such as PEG 8000 preferred" for this purpose.

There are references in the patent art to PEGs with slightly lower molecular weights being used as granulation aids. U.S. Pat. No. 5,403,593 teaches PEGs with molecular weight as low as about 3000 (Col. 5, line 19 and Claim 3) for this purpose. Although no clear reason or data is presented in the patent, Claim 2 includes PEG with "average molecular weight of at least 900" as part of a granulating medium. As noted at column 2, line 64, "the compositions of the invention are prepared by a melt granulation process, in the substantial absence of added liquid solvents". Examples 1 and 2 note that tablets made from inventive granulations have low friability (column 9, line 51; column 10, line 47). However, it is not possible for one skilled in the art to infer that this performance can be caused by low MW PEG, as the example compositions only contain PEG 8000.

U.S. Patent Publication No. 2011/0112160, at Claim 6, describes a tablet with an excipient comprising PEG with MW in the range of 400 to 20,000. None of the examples of this application include PEGs with MW lower than 4000. Although the application states that acceptable friability can be achieved (P0023, P0051) using this technology, no data is given that would allow someone skilled in the art to learn low MW PEG's ability to affect this property. In fact, P0053 explicitly states that PEG 4000 is preferred.

U.S. Patent Publication No. 2011/0135738 is similar to the above application. It names the same inventors and has the same assignee. Like the previous application, the use of PEG 400 in a tablet is recited (Claim 2). Also like the above application, there is no teaching that would enable one skilled in the art to use low molecular PEG as a friability improver. Again, PEG-4000 is explicitly taught as the preferred material (P0053).

U.S. Patent Publication No. 2011/0136883 (same assignee as above two (2) references, one common inventor) speaks directly to use of PEG-400 in tablet formulations. This reference is not predictive of the instant invention. While Example 4 (Table 2) teaches the use of PEG 400 at five percent (5%), the test results shown in Table 4 do not exhibit the dramatic decrease in friability discovered in our invention. The Application's data shows a drop in friability (0.10% without PEG 400, 0.05% with it) and a decrease in hardness (140-220 N without PEG-400, 110-130 with it). Tablets prepared according to our invention do not exhibit the loss in hardness. More importantly, our discovery is that low MW PEG has a much greater impact on friability at much lower levels than taught here. In fact, we are not even able to make acceptable tablets when PEG 400 is utilized at five percent (5%).

U.S. Patent Publication No. 2011/0262497 (same inventor and assignee as immediate above application) mentions the use of liquid polyethylene glycols as a possible excipient at P0029. However there is no teaching anywhere in this application as to the benefits and/or functions of doing so.

U.S. Pat. No. 4,093,710 is directed to the preparation of powders or granules of small size, smaller than 20 mesh (a higher mesh number means a smaller sized particle). This patent refers to the use of a surfactant for use in the granulating solution employed. The surfactant may be polyethylene glycol of PEG 400-PEG 9000, as well as other surfactants such as sodium lauryl sulfate. PEG 1540 is identified as the preferred surfactant. As this patent is directed to the preparation of free flowing, rapidly dissolving powders or small granules, friability and related properties are not discussed.

SUMMARY OF THE INVENTION

We have discovered that low molecular polyethylene glycols can dramatically improve the friability of tablet formulations when incorporated at surprisingly low levels. In particular, polyethylene glycols in the range of about PEG 200 to about PEG 1000 give superior performance and improvement in friability, without a significant loss in hardness or other properties, when formulating tablets in otherwise customary fashion. The level of incorporation of low molecular weight and similar compounds at low weight percentage gives improvements that are particularly surprising. In fact, at weight levels of the overall tablet weight at about 0.1-about 5.0%, striking improvements in friability are observed. At higher levels, above about five percent (5.0% w/weight of the tablet) an unacceptable loss of hardness is observed. Hardness of a tablet is impacted by a wide variety of factors, one of which is the character of the central or active agent of the tablet, as well as the excipients included therewith. As a result, an absolute standard or range for hardness of the tablets of the invention is difficult to establish. The tablets of this invention have reduced friability and exhibit at least eighty percent (80%) of the hardness the same tablet would exhibit in the absence of the agent to reduce friability. The hardness exhibited by the tablets of this invention may be 85, 90, 95 or even 100% of the hardness of the same tablet made without the friability reducing agent.

While polyethylene glycol of the molecular weight PEG 200-PEG 1000 is the preferred friability improvement agent of this invention, other similar compounds are effective in improving friability (resistance to crumbling) without sacrificing other desirable properties. In addition to polyethylene glycol, other glycols, such as polypropylene glycol and methoxypolyethylene glycol at relatively low molecular weights (PPG 425-about PPG 1000; MPEG 350-about MPEG 1000) are also effective in improving tablet friability at less than about five percent (5.0%) by weight. Other high hydroxide content materials that are at least partially water soluble, like glycerin and Tween® 80 are also effective in this role.

The invention therefor is focused not on powders or granules, but on tablets (tablet diameter is typically at least ¾ inch diameter), and in particular, tablets of low friability, tablets that exhibit a resistance to crumbling or breakage or chipping. The tablets require an active agent of some sort—the agent that is being delivered to the consumer in the tablet dosage. This might be a flavor, an aroma, a medication (e.g., pharmaceutical prescription or OTC, a gastric acid neutralizer, a laxative, an anti-flatulent, etc.) a nutritional product, a bleach, a detergent, an herbicide or insecticide or bactericide, or any other agent that is to be consumed or used. In preferred embodiments, the tablet may comprise more than one active agent.

Typically, the tablet will also include an excipient of some type, to aid in delivery of the desired active agent. Excipients are widely known, and can be selected from any chemical class that does not impact the desired physical properties of the tablet. Many excipients are stabilizers and add bulk to the tablet, and may function as binders, such as saccharides and polysaccharides, sugar alcohols such as sorbitol or xylitol, dicalcium phosphate, microcrystalline cellulose, various proteins and synthetic polymers. Other excipients commonly employed in the tablet art are lubricants, coatings and disintegrants, all of which are compatible with the friability reducing agents of the invention. Many excipients are featured in the examples set forth below, but are not so limited, and excipients as would be recognized as commonly useful in the preparation of tablets by those of skill in that art may be generally useful in the invention. The tablet need not effervesce or otherwise demonstrate active properties other than dissolution on wetting, but in one embodiment, the tablet does comprise a dry effervescent couple (typically, an organic acid like citric, fumaric or malic acid together with a carbonate or bicarbonate such as sodium or potassium bicarbonate) that will generate carbon dioxide when the tablet is wetted, or preferably immersed, such as a drink or bathing formulation.

Thus, the invention is focused in terms of the properties of the additive to reduce friability, but otherwise generally inclusive of the components and purposes to which tablets are commonly put. The tablet generally includes an active agent of some type, and an excipient chosen to be compatible with that active agent. The excipient may improve shape, appearance, flavor, texture or other features of the tablet. A wide variety of optional agents, depending on the ultimate utility of the tablet, may be incorporated. These include flavorants, colorants, aromatic agents, dispersants, preservatives, lubricants, etc. The tablets of the invention further comprise an agent to reduce friability upon tableting, present in amounts of about 0.1-about 5.0 percent by weight of a compound having a solubility in room temperature water of at least eighty percent (80%) (w/w %) and is comprised of at least three percent (3%) by weight —OH moieties, and wherein said tablet with said friability reducing agent exhibits a hardness of at least eighty percent (80%) of the hardness of that same tablet prepared in the absence of said additive.

SPECIFIC EXAMPLES OF THE INVENTION

The following examples demonstrate this performance. The examples are provided for purposes of demonstration only, and are not intended to limit the invention in any way. Other active agents and excipients, as well as other agents effective in reducing friability, within the broad parameters set forth above, will occur to those of skill in the art.

Example 1

Denture Cleanser Tablet

The following base denture cleanser formula was prepared by blending the indicated ingredients (Table 1) using conventional powder mixing equipment.

TABLE 1

| Material | % w/w |
|---|---|
| Sodium Bicarbonate | 25.0 |
| Citric Acid | 20.0 |
| Sodium Carbonate | 15.0 |
| Potassium Monopersulfate | 10.0 |
| Sodium Perborate Monohydrate | 10.0 |
| Maltodextrin | 9.5 |
| Sodium Sulfate | 8.7 |
| Sodium Lauryl Sulfoacetate | 0.7 |
| PEG 8000 | 0.7 |
| Flavor Oil | 0.3 |
| Sodium Benzoate | 0.1 |
| Total | 100.0 |

Formulations that demonstrate the invention were prepared by adding the indicated amount of PEG 400. The formulas were balanced to one hundred percent (100%) by reducing the amount of sodium sulfate.

Tablets were compressed using ⅞" round tooling on a Stokes F press. Compression force was adjusted to give the hardest possible tablet (limit set by capability of the press or by the appearance of tablet capping). Data is shown in Table 2.

Hardness was measured using a Schuleuniger-4M tablet hardness tester.

Friability was measured in a manner similar to that described in the USP-NF, Chapter <1216>. The USP-NF method was modified in that the number of tablet used and the method of calculation were changed as indicated here. Ten (10) tablets were placed in an Erweka TA friability apparatus. The tablets were tumbled at 25 rpm for the indicated number of minutes. The percentage of unbroken tablets is reported.

Dissolution time was measured by placing a tablet in 125 ml of water at 25° C. The time needed for essentially complete dissolution is reported.

TABLE 2

| PEG 400 concentration | Weight (g) | Hardness (kp) | Thickness (mm) | Friability (% whole tablets) | | | | | Dissolution Time (sec) |
|---|---|---|---|---|---|---|---|---|---|
| | | | | 2 min | 4 min | 6 min | 8 min | 10 min | |
| 0% | 2.69 | 7.8 | 3.96 | 70 | 10 | 0 | 0 | 0 | 83 |
| 0.1% | 2.70 | 8.2 | 3.95 | 100 | 85 | 40 | 15 | 5 | 82 |
| 0.6% | 2.69 | 9.0 | 3.82 | 100 | 100 | 100 | 100 | 100 | 103 |
| 1.0% | 2.65 | 8.5 | 3.85 | 100 | 100 | 100 | 100 | 100 | 145 |
| 5.0% | 2.80 | 4.6 | 4.21 | 100 | 100 | 100 | 100 | 100 | 71 |

This data clearly shows the effect of PEG 400 on the denture cleanser composition. Below five percent (5%) PEG 400, friability is unexpectedly and dramatically improved while hardness and dissolution time are not significantly affected. At five percent (5%) though, the tablet's hardness is decreased to an unacceptable level.

Example 2

Alternate Molecular Weight PEGs

The effect of different molecular weight PEGs was investigated. The PEGs listed in Table 3 were evaluated using the formula shown in Table 1. 0.6% PEG was used in each trial. The formulas were balanced to 100% by reducing sodium sulfate. Data is shown below.

TABLE 3

| PEG MW | Weight (g) | Hardness (kp) | Thickness (mm) | Friability (% whole Tablets) | | | | | Dissolution Time (sec) |
|---|---|---|---|---|---|---|---|---|---|
| | | | | 2 min | 4 min | 6 min | 8 min | 10 min | |
| None (control) | 2.69 | 7.8 | 3.96 | 70 | 10 | 0 | 0 | 0 | 83 |
| 200 | 2.66 | 8.1 | 3.92 | 100 | 100 | 100 | 100 | 100 | 72 |
| 400 | 2.69 | 9.0 | 3.82 | 100 | 100 | 100 | 100 | 100 | 103 |
| 600 | 2.69 | 7.5 | 3.94 | 100 | 100 | 100 | 100 | 100 | 145 |
| 1000 | 2.71 | 7.4 | 3.98 | 100 | 85 | 30 | 0 | 0 | 82 |
| 1450 | 2.62 | 6.6 | 3.90 | 60 | 20 | 5 | 0 | 0 | 73 |

Clearly, the friability benefit of the invention is maximized when using PEGs with MW between 200 and 1,000. The drop in performance at MW 1450 is surprising.

Example 3

Alternate Materials Similar in Structure to PEG

Materials with chemical structures somewhat similar to PEG were tested to assess their performance in reducing tablet friability. That is, we assessed hydrophilic materials that are ethoxylated or propoxylated. A range of chain length materials were investigated. For comparison purposes, we also looked at a hydrophobic material (mineral oil) and glycerin (as a very short chain, high hydroxyl content material). These assessments were conducted using the denture cleanser formulation shown in Table 1.

Data from these experiments are presented in Table 4:

TABLE 4

| Material added (0.6% formula) | Structure | Weight (g) | Hardness (kp) | Friability (% Whole Tablets) | | | | |
|---|---|---|---|---|---|---|---|---|
| | | | | 2 min | 4 min | 6 min | 8 min | 10 min |
| No additive | — | 2.69 | 7.8 | 70 | 10 | 0 | 0 | 0 |
| PEG 400 | H—(O—CH$_2$—CH$_2$)$_8$—OH | 2.69 | 9.0 | 100 | 100 | 100 | 100 | 100 |
| Polypropylene glycol 250 (PPG-4) | H—(O—CH(CH$_3$)CH$_2$)$_4$—OH | 2.64 | 8.0 | 100 | 100 | 100 | 100 | 100 |
| Polypropylene glycol 425 (PPG-9) | H—(O—CH(CH$_3$)—CH$_2$)$_9$—OH | 2.67 | 7.5 | 100 | 80 | 55 | 30 | 0 |
| Polypropylene glycol 700 (PPG-10) | H—(O—CH(CH$_3$)—CH$_2$)$_{10}$—OH | 2.65 | 6.5 | 100 | 70 | 30 | 10 | 0 |
| Polypropylene glycol 2000 (PPG-26) | H—(O—CH(CH$_3$)—CH$_2$)$_{26}$—OH | 2.67 | 3.7 | 20 | 0 | 0 | 0 | 0 |
| Methoxypolyethylene glycol 350 (MPEG-6) | CH$_3$—(O—CH$_2$—CH$_2$)$_6$—OH | 2.66 | 6.4 | 100 | 100 | 100 | 100 | 100 |

TABLE 4-continued

| Material added (0.6% formula) | Structure | Weight (g) | Hardness (kp) | Friability (% Whole Tablets) | | | | |
|---|---|---|---|---|---|---|---|---|
| | | | | 2 min | 4 min | 6 min | 8 min | 10 min |
| Methoxypolyethylene glycol 550 (MPEG-10) | $CH_3-(O-CH_2-CH_2)_{10}-OH$ | 2.66 | 6.4 | 100 | 100 | 100 | 100 | 100 |
| Tween 80 (Polysorbate 80) | 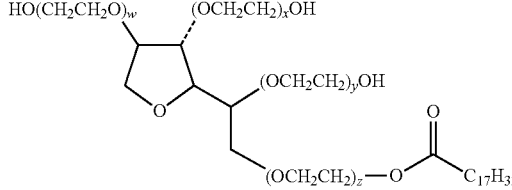  Polysorbate 80 (Sum of w, x, y, and z is 20) | 2.69 | 5.6 | 100 | 100 | 90 | 95 | 85 |
| Mineral Oil | $C_nH_{2n+2}$ $n=12\text{-}40$ | 2.65 | 7.4 | 90 | 60 | 30 | 0 | 0 |
| Glycerin | $OH-CH_2-C(OH)-CH_2-OH$ | 2.65 | 9.5 | 100 | 100 | 100 | 100 | 100 |

In an attempt to understand what chemical properties of the tested materials are critical to improving friability, we looked at some of the physical properties of the tested materials. Table 5 provides these comparisons:

TABLE 5

| Material | Friability improvement | Solubility in Water (w/w %) | Appearance at Room Temperature |
|---|---|---|---|
| PEG 200 | Yes | 100% | Clear viscous liquid |
| PEG 400 | Yes | 100% | Clear viscous liquid |
| PEG 600 | Yes | 100% | Clear viscous liquid |
| PEG 1000 | Somewhat | 80% | Soft, Opaque white solid |
| PEG 1450 | No | 72% | Soft, Opaque white solid |
| MPEG 350 | Yes | 100% | Clear viscous liquid |
| MPEG 550 | Yes | 100% | Clear viscous liquid |
| PPG 250 | Yes | 100% | Clear viscous liquid |
| PPG 425 | Yes | Soluble at room temperature, but insoluble at higher temperatures | Clear viscous liquid |
| PPG 700 | Somewhat | Soluble to slightly soluble at room temperature | Clear viscous liquid |
| PPG 2000 | No | 0% | Clear viscous liquid |
| Tween 80 | Yes | 100% | Clear viscous liquid (yellow) |
| Mineral Oil | No | 0% | Clear viscous liquid |
| Glycerin | Yes | 100% | Clear viscous liquid |

Examining these data, it appears that agents which are at least somewhat soluble in water at room temperature exhibit the inventive effect. It will be evident that the friability reducing agents of this invention are physically and chemically compatible with each other. Accordingly, they may be used in combination and in mixtures. Given the desirability of limiting the amount of the friability reducing agent present in the tablet in general, the Examples herein focus on one agent or another, but multiple agents could be used together, provided the weight limits are observed, and any reduction in hardness is controlled Example 4

Acids Other than Citric Acid

Denture cleanser tablets formulated according to Table 1, with PEG 400 at included at the indicated level were produced with acids other than citric acid. This was done to ascertain if the inventive effect is limited to products based only on citric acid. Table 6 displays the results of this experiment:

TABLE 6

| Acid | PEG 400 level (%) | Weight (g) | Hardness (kp) | Friability (% Whole Tablets) | | | | |
|---|---|---|---|---|---|---|---|---|
| | | | | 2 min | 4 min | 6 min | 8 min | 10 min |
| Citric Acid | 0 | 2.69 | 7.77 | 70 | 10 | 0 | 0 | 0 |
| Citric Acid | 0.6 | 2.69 | 8.96 | 100 | 100 | 100 | 100 | 100 |
| Fumaric Acid | 0 | 2.61 | 5.09 | 25 | 0 | 0 | 0 | 0 |

TABLE 6-continued

| Acid | PEG 400 level (%) | Weight (g) | Hardness (kp) | Friability (% Whole Tablets) | | | | |
|---|---|---|---|---|---|---|---|---|
| | | | | 2 min | 4 min | 6 min | 8 min | 10 min |
| Fumaric Acid | 0.6 | 2.60 | 5.80 | 100 | 100 | 95 | 90 | 85 |
| Malic Acid | 0 | n/a | n/a | — | — | — | — | — |
| Malic Acid | 0.6 | 2.39 | 5.28 | 100 | 100 | 100 | 100 | 100 |
| Sodium Bisulfate | 0 | 2.66 | 6.56 | 10 | 0 | 0 | 0 | 0 |
| Sodium Bisulfate | 0.6 | 2.70 | 5.99 | 85 | 40 | 10 | 0 | 0 |

The above data clearly show the benefits of including PEG 400 in the formulation. Most notably, and surprisingly, tablets made with malic acid could not be produced without inclusion of the low molecular weight PEG.

Product formulations other than denture tablets were also studied. Examples follow.

Example 5

Vitamin C Drink Tablet

An effervescent Vitamin C tablet (designed to dissolve in water before ingesting) was developed using the composition shown in Table 7. The formula was prepared by blending the indicated ingredients using conventional powder mixing equipment.

TABLE 7

| Material | % w/w |
|---|---|
| Ascorbic Acid | 33.4 |
| Citric Acid | 33.4 |
| Sodium Bicarbonate | 8.3 |
| Potassium Bicarbonate | 8.3 |
| Sorbitol | 8.6 |
| Maltodextrin | 2.0 |
| Flavor Oil | 0.2 |
| Sucralose | 0.4 |
| PEG 8000 | 4.4 |
| Sodium Benzoate | 1.0 |
| Total | 100.0 |

Formulations that demonstrate the invention were prepared by adding the indicated amount of PEG 400. The formulas were balanced to one hundred percent (100%) by reducing the amount of sorbitol.

Three (3) gram tablets were compressed using 7/8" round tooling on a Stokes F press. Compression force was adjusted to give the hardest possible tablet (limit set by capability of the press or by appearance of tablet capping).

These tablets were evaluated by the same methods discussed above. Data are shown in Table 8.

Again, the addition of a small amount of PEG 400 provides the unexpected result of highly improved friability without harm to other properties.

Example 6

Beverage Tablet

An effervescent tablet designed to form a lemon/lime beverage when dissolved in water was formulated as shown in Table 9:

TABLE 9

| Material | % w/w |
|---|---|
| Citric Acid | 54.6 |
| Sodium Bicarbonate | 21.2 |
| Sorbitol | 17.7 |
| Lemon/Lime Flavor Oil | 0.9 |
| Acesulfame K | 0.4 |
| Aspartame | 1.0 |
| PEG 8000 | 2.7 |
| Sodium Benzoate | 1.5 |
| Total | 100.0 |

Formulations that demonstrate the invention were prepared by adding the indicated amount of PEG 400. The formulas were balanced to one hundred percent (100%) by reducing the amount of sorbitol.

3.3 gram tablets were compressed using 7/8" round tooling on a Stokes F press. As above, compression force was adjusted to give the hardest possible tablet (limit set by capability of the press or by appearance of tablet capping).

These tablets were evaluated by the same methods discussed above. Data are shown in Table 10.

TABLE 8

| PEG 400 concentration | Weight (g) | Hardness (kp) | Thickness (mm) | Friability (% Whole Tablets) | | | | | Comments |
|---|---|---|---|---|---|---|---|---|---|
| | | | | 2 min | 4 min | 6 min | 8 min | 10 min | |
| 0 | 2.95 | 5.4 | 5.03 | 50 | 0 | 0 | 0 | 0 | — |
| 0.1% | 2.99 | 6.1 | 5.06 | 100 | 95 | 60 | 25 | 5 | — |
| 0.6% | 2.92 | 6.7 | 4.92 | 100 | 100 | 100 | 100 | 100 | — |
| 1.0% | 2.78 | 3.7 | 5.05 | 100 | 100 | 100 | 100 | 100 | — |
| 5.0% | — | — | — | — | — | — | — | — | Tablets could not be pressed due to punch face sticking and sidewall scoring |

TABLE 10

| PEG 400 concentration | Weight (g) | Hardness (kp) | Thickness (mm) | Friability (% Whole Tablets) | | | | |
|---|---|---|---|---|---|---|---|---|
| | | | | 2 min | 4 min | 6 min | 8 min | 10 min |
| 0 | 3.27 | 7.1 | 5.60 | 100 | 75 | 35 | 0 | 0 |
| 0.6% | 3.27 | 7.7 | 5.55 | 100 | 100 | 100 | 100 | 100 |

Again, the dramatic effect of low molecular weight PEG addition was demonstrated.

It may be noted that all of the formulations in the above examples are effervescent. That is, they contain one or more organic acids and one or more carbonate salts. In the presence of water the acid and the carbonate salt react to release carbon dioxide, creating a bubbling action that is appealing to consumers and that disperses formula ingredients. Many examples of effervescent products (developed for many reasons) can be found in the art. Given that effervescent formulations are somewhat specialized, our inventive technology was also checked in a non-effervescent formulation.

Example 7

Candy Tablet

A tart, sugar based candy tablet was developed according to the formula shown in Table 11. This tablet can be dissolved in the mouth as a lozenge.

TABLE 11

| Material | % w/w |
|---|---|
| Dextrose | 44.7 |
| Maltodextrin | 44.4 |
| Citric Acid | 10.0 |
| Lemon/Lime Flavor Oil | 0.3 |
| PEG 8000 | 0.5 |
| Sodium Benzoate | 0.1 |
| Total | 100.0 |

Formulations that demonstrate the invention were prepared by adding the indicated amount of PEG 400. The formulas were balanced to one hundred percent (100%) by reducing the amount of maltodextrin.

2.5 gram tablets were compressed using ⅞" round tooling on a Stokes F press. As above, compression force was adjusted to give the hardest possible tablet (limit set by capability of the press or by appearance of tablet capping).

These tablets were evaluated by the same methods discussed above. Data are shown in Table 12.

These data clearly demonstrate the benefits of the invention in a non-effervescent formulation.

While the present invention has been disclosed with references to certain embodiments, numerous modification, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A denture cleanser in the form of a compressed tablet exhibiting reduced friability, wherein said denture cleanser comprises a bleach, an excipient compatible with said bleach, and an agent to reduce friability, wherein said agent to reduce friability is PEG-400 present in amounts of about 0.1%-0.6% by weight of the tablet, said compressed tablet exhibits a hardness of at least 4.7 kp and wherein said compressed tablet comprising said PEG-400 exhibits a hardness of at least eighty percent (80%) of the hardness exhibited by said compressed tablet prepared in the absence of said PEG-400.

2. The denture cleanser compressed tablet of claim 1, wherein said tablet comprises an effervescent couple which combine to release carbon dioxide when the tablet is moistened.

3. The denture cleanser compressed tablet of claim 1, wherein said active agent comprises an aroma.

4. The denture cleanser compressed tablet of claim 1, wherein said excipient is a stabilizer, lubricant, a binder, a disintegrant, or a coating.

5. The denture cleanser compressed tablet of claim 2, wherein said effervescent couple comprises sodium bicarbonate and acid selected from the group consisting of citric acid, fumaric acid, malic acid and mixtures thereof.

6. The denture cleanser compressed tablet of claim 5, wherein said acid comprises citric acid.

7. The denture cleanser of claim 1 wherein said denture cleanser comprises a detergent.

8. The denture cleanser compressed tablet of claim 1, wherein said bleach is a carbonate, persulfate or perborate.

* * * * *

TABLE 12

| PEG 400 concentration | Weight (g) | Hardness (kp) | Thickness (mm) | Friability (% Whole Tablets) | | | | | Comments |
|---|---|---|---|---|---|---|---|---|---|
| | | | | 2 min | 4 min | 6 min | 8 min | 10 min | |
| 0 | 2.38 | 5.8 | 4.66 | 40 | 0 | 0 | 0 | 0 | — |
| 0.1% | 2.37 | 4.7 | 4.58 | 70 | 35 | 5 | 0 | 0 | — |
| 0.6% | 2.40 | 6.0 | 4.61 | 100 | 100 | 100 | 85 | 75 | — |
| 1.0% | — | — | — | — | — | — | — | — | Flow issues. Tablets were not pressed |